United States Patent [19]
Abel et al.

[11] Patent Number: 6,114,571
[45] Date of Patent: Sep. 5, 2000

[54] PALLADIUM, GOLD AND BORON CATALYST AND PROCESS FOR THE PREPARATION OF VINYL ACETATE

[75] Inventors: Roland Abel; Ioan Nicolau, both of Corpus Christi, Tex.; Erich Hopf, Grundau; Rainer Kiemel, Erlensee, both of Germany

[73] Assignee: Celanese GmbH, Germany

[21] Appl. No.: 09/155,442

[22] PCT Filed: Mar. 17, 1997

[86] PCT No.: PCT/EP97/01327

§ 371 Date: Nov. 2, 1998

§ 102(e) Date: Nov. 2, 1998

[87] PCT Pub. No.: WO97/37759

PCT Pub. Date: Oct. 16, 1997

[30] Foreign Application Priority Data

Apr. 4, 1996 [DE] Germany .............................. 196 13 791

[51] Int. Cl.$^7$ .............................. C07C 67/05; B01J 31/00
[52] U.S. Cl. ........................... 560/245; 502/102; 502/103; 502/202; 502/207
[58] Field of Search ..................................... 502/102, 103, 502/207, 202; 560/245

[56] References Cited

U.S. PATENT DOCUMENTS

| | | |
|---|---|---|
| 3,743,607 | 7/1973 | Sennewald et al. . |
| 3,939,199 | 2/1976 | Fernholz et al. . |
| 4,048,096 | 9/1977 | Bissot . |
| 5,332,710 | 7/1994 | Nicolau et al. . |
| 5,688,993 | 11/1997 | Provine et al. . |

FOREIGN PATENT DOCUMENTS

| | | |
|---|---|---|
| 0672453 | 9/1995 | European Pat. Off. . |
| 0685451 | 12/1995 | European Pat. Off. . |

*Primary Examiner*—Gary Geist
*Assistant Examiner*—Robert W. Deemie
*Attorney, Agent, or Firm*—Bierman, Muserlian and Lucas

[57] ABSTRACT

A catalyst for preparing vinyl acetate in the gas phase from ethylene, acetic acid and oxygen or oxygen-containing gases with, at the same time, low-high boiler formation which catalyst comprises palladium and/or its compounds, gold and/or its compounds, moron or boron compounds and alkali metal compounds on a particular support.

10 Claims, No Drawings

PALLADIUM, GOLD AND BORON CATALYST AND PROCESS FOR THE PREPARATION OF VINYL ACETATE

STATE OF THE ART

The present invention relates to a catalyst comprising palladium, gold and an alkali metal compound, a process for its preparation and its use for preparing vinyl acetate from acetic acid, ethylene and oxygen or oxygen-containing gases.

It is known from the prior art that vinyl acetate can be prepared from ethylene, oxygen and acetic acid by reaction over catalysts comprising palladium, gold and an alkali metal compound on a support material (for instance silicon dioxide). Such catalysts display good activity and generally form little carbon dioxide and ethyl acetate. Although high-boilers are formed as further by-products in amounts which appear to be small, they nevertheless present a problem from process and ecological points of view. The term high-boilers here refers to, in particular, the compounds ethylidene diacetate, ethylene glycol and diacetoxyethylenes.

Literature references which disclose the preparation of such catalysts for the commercial production of vinyl acetate generally describe methods of depositing the noble metals in a shell on the catalyst support.

U.S. Pat. No. 4,048,096 describes the preparation of a catalyst for vinyl acetate production in which the dissolved noble metal salts are adsorbed by the support from a solution which has the same volume as the pores of the support material, with the support particles being agitated in a rotating vessel. The salts are then fixed using alkalis, without drying the support beforehand.

U.S. Pat. No. 5,332,710 discloses the preparation of a catalyst for vinyl acetate production where the insoluble noble metal salts are precipitated onto the support particles by agitating these in a rotating drum for at least half an hour during the precipitation by means of alkalis.

THE INVENTION

It has now surprisingly been found that the addition of boron or boron compounds improves the selectivity of the catalyst, with, in particular, the formation of high-boilers being significantly reduced. High-boilers are, in particular, the compounds mentioned in the introduction.

The invention provides a catalyst for preparing vinyl acetate in the gas phase from ethylene, acetic acid and oxygen or oxygen-containing gases with, at the same time, low high-boiler formation, which catalyst comprises palladium and/or its compounds, gold and/or its compounds and alkali metal compounds on a particulate support, wherein the catalyst further comprises boron or boron compounds.

In a preferred embodiment, the catalyst is prepared by a) impregnating the support with soluble palladium and gold compounds;

b) converting the soluble palladium and gold compounds on the support into insoluble compounds by means of an alkaline solution;

c) reducing the insoluble palladium and gold compounds on the support by means of a reducing agent in the liquid phase;

d) washing and subsequently drying the support;

e) impregnating the support with a soluble alkali metal compound; and f) finally drying the support at a maximum of 150° C.

The invention also relates to a process for preparing vinyl acetate in the gas phase from ethylene, acetic acid and oxygen or oxygen-containing gases while at the same time, there is a low boiler formation over a catalyst as defined above.

The invention accordingly provides, on the one hand, a process for preparing a catalyst for the production of vinyl acetate in the gas phase from ethylene, acetic acid and oxygen or oxygen-containing gases with, at the same time, low high-boiler formation, which catalyst comprises palladium and/or its compounds, gold and/or its compounds and alkali metal compounds on a particulate support, where the catalyst is prepared by a) impregnating the support with soluble palladium and gold compounds;

b) converting the soluble palladium and gold compounds on the support into insoluble compounds by means of an alkaline solution;

c) reducing the insoluble palladium and gold compounds on the support by means of a reducing agent in the liquid phase;

d) washing and subsequently drying the support;

e) impregnating the support with a soluble alkali metal compound; and f) finally drying the support at a maximum of 150° C., wherein boron or boron compounds are applied to the catalyst prior to the final drying.

On the other hand, the invention provides a process for preparing vinyl acetate in the gas phase from ethylene, acetic acid and oxygen or oxygen-containing gases with, at the same time, low high-boiler formation over the catalyst of the invention.

The boron content of the catalyst is preferably from 0.01 to 1 % by weight, in particular from 0.01 to 0.2% by weight. The boron is applied to the support in the form of its compounds, preferably in the form of borates. The application can be carried out in the abovementioned step a) together with the soluble palladium and gold compounds, in step b) together with the alkaline solution, or using a borate solution as alkaline solution, in step e) together with the soluble alkali metal compound or in a separate step before the final drying of the support. Preference is given to application in step b).

The support particles of the catalyst of the invention can have any geometric shape, for example the shape of spheres, tablets or cylinders of regular or irregular type. The dimensions of the support particles are generally between 1 and 8 mm. Preference is given to a spherical shape, for example spheres having a diameter of from 4 to 8 mm. The support particles are generally termed pellets.

Suitable supports are the known inert support materials such as silica, aluminum oxide, aluminosilicates, silicates, titanium oxide, zirconium oxide, titanates, silicon carbide and carbon. Particularly suitable supports are supports of this type having a specific surface area of from 50 to 300 $m^2/g$ (measured by the BET method) and a mean pore radius of from 50 to 2000 Å (measured using mercury porosimetry), especially silica ($SiO_2$) and $SiO_2/Al_2O_3$ mixtures.

The total pore volume of the support is preferably from 0.4 to 1.2 ml/g. Less than 10% of this volume should be made up by "micropores" having a pore diameter of less than 30 Å (Ångström). Such supports can be prepared from aerogenic $SiO_2$ or an aerogenic $SiO_2Al_2O_3$ mixture in the form of vitreous microspheres which can be prepared, for example, by flame hydrolysis of silicon tetrachloride or a silicon tetrachloride/aluminum trichloride mixture in an oxyhydrogen flame (U.S. Pat. No. 3,939,199). These microspheres are commercially available under the name ®Aerosil or ®Cabosil.

The dissolved gold and palladium salts are adsorbed in the pores of the support material, which is referred to in the prior art as the pore volume impregnation method. The supports impregnated in this way are treated with an alkaline solution, with the use of a borate solution being preferred, in order to deposit the noble metals as insoluble compounds. These compounds are subsequently subjected to a reductive treatment, with the reducing agent being present in the liquid phase.

Suitable solvents for the catalytically active substances are, in particular, water or unsubstituted carboxylic acids having from 2 to 10 carbon atoms, for example acetic acid, propionic acid, n- and iso-butyric acid and the various valeric acids. Owing to its physical properties and also for economic reasons, acetic acid is preferably used as the carboxylic acid. The additional use of an inert solvent is advantageous when the carboxylic acid used is one in which the substances are not sufficiently soluble. Thus, for example, palladium chloride dissolves significantly better in an aqueous acetic acid than in glacial acetic acid. Suitable additional solvents are those which are inert and miscible with the carboxylic acid, for example water or ethers such as tetrahydrofuran or dioxane, but also hydrocarbons such as benzene.

Two suitable methods for preparing the catalyst of the invention, designated by I and II, are described below. A particular step in method II can be carried out in two variants A) and B).

In method I, soluble gold and palladium salts are dissolved in such an amount of solvent that the solution volume corresponds to about 90–110% of the pore volume of the support material. Palladium(II) chloride, sodium palladium (II) chloride and palladium(II) nitrate are examples of suitable soluble palladium compounds, and gold(III) chloride, tetrachloroauric(III) acid and its alkali metal salts can be used as soluble gold compounds. In general, the amounts of these compounds used are such that the finished catalyst contains between about 2 and about 14 g/l, preferably between 4 and 8 g/l, of palladium and between about 1 and about 8 g/l, preferably between 2 and 5 g/l, of gold. Accordingly, the gold content of the catalyst is generally from about 10 to 70% of the mass of palladium present therein.

The solution is adsorbed in the support and the metals are fixed by placing the support for a sufficient length of time in an alkaline solution which has a sufficiently high concentration to precipitate the insoluble metal salts. The fixing step b) can be carried out by immersing the impregnated supports in sufficiently alkaline fixing solution for them to be completely covered, with the support particles preferably being agitated, for instance as described in U.S. Pat. No. 5,332,710. This method is hereby incorporated by reference. According to U.S. Pat. No. 5,332,710, the impregnated support materials are immersed in an alkaline solution and agitated by rotation from the commencement of the deposition of the insoluble noble metal compounds. This rotation of the support particles in the alkaline solution should be continued for at least half an hour from the start of the treatment, preferably one hour. Rotation and immersion can be for up to 4 hours. The treated support particles can then be left at rest in the fixing solution in order to ensure that complete precipitation of the noble metal compounds occurs. The alkaline fixing solution can be any solution which is able to precipitate gold and palladium; preference is given to using borate solutions.

Any type of rotation or similar treatment which keeps the support particles in motion can be used, since the precise method is not critical. However, the intensity of the agitation is important. This should be sufficient uniformly to wet the entire surface of the impregnated supports with the alkaline fixing solution. The agitation of the support particles must not be so vigorous that the insoluble noble metal compounds are lost as a result, i.e. that they are rubbed off the support surface. The rotation rate should preferably be from 1 to 20 revolutions per minute, but it can also be greater depending on the type of support material and the amount of noble metal to be deposited. Different rotation rates can be selected and the rotation rate also depends on the apparatus used, the size and shape of the supports, the type of support, the metal impregnation, etc., but should correspond approximately to the abovementioned rotation rates.

The fixing solution is an alkaline solution, preferably an aqueous solution, containing boron compounds. Particular preference is given to using aqueous solutions of borax, potassium tetraborate or mixtures of alkali metal hydroxide solution and boric acid. The alkaline solution can have buffering properties.

The steps c) to f) are then carried out.

In method II, a suitable catalyst support is first impregnated with a solution containing soluble palladium and gold compounds. Separate solutions of palladium and gold compounds can also be used in succession, although a drying step then has to be carried out in between. For effective impregnation, the volume of the impregnation solution should be from 95 to 100% of the pore volume of the catalyst support, preferably 98–99%. After impregnation of the support with the soluble palladium and gold compounds, the impregnated support is dried before the palladium and gold compounds are fixed as insoluble compounds. The fixing step comprises at least two separate stages of treatment with the alkaline fixing solution. In each of these stages, the amount of the alkaline reagent used is at most equal to the amount required to react with the total amount of the soluble noble metal salts present on the support. This amount can be greater than the amount stoichiometrically required for the reaction. The amount of the alkaline reagent employed in each fixing stage is preferably less than the amount required for complete reaction with the soluble noble metal salts. The first fixing stage is carried out by bringing the impregnated and then dried support in contact with the alkaline fixing solution. The volume of the fixing solution corresponds to the pore volume of the dry support material. The amount of the alkaline compound present therein should be such that the molar ratio of alkali metal from the alkaline compound to anions from the soluble metal salt is from 0.7:1 to 2:1, and the volume of the solution should correspond to the absorption capacity of the support in the dry state. The alkaline fixing solution is poured onto the agitated support particles in order to be absorbed and the support particles are allowed to stand for up to 24 hours, preferably from 2 to 8 hours.

The second fixing stage can be carried out in 2 variants A) and B).

Variant A) is carried out by treating the undried support particles with a second fixing solution. In this solution, the molar ratio of alkali metal from the alkaline compound to anion from the metal salt is from about 0.2:1 to 2:1. The solution volume should at least just cover the supports. The treatment of the support particles with the second fixing solution should be for a time of up to 16 hours, at least 2 hours, preferably at least 4 hours.

In variant B), the supports are treated using the rotation-immersion process according to U.S. Pat. No. 5,332,710. In this process, the supports previously fixed in the first stage are immersed in the alkaline fixing solution of the second stage and maintained in rotary motion therein during the initial phase of the second stage. This rotation should be for a time of at least half an hour, preferably one hour. The treatment can be for up to 4 hours before the supports are allowed to stand in the fixing solution in order to ensure complete deposition. Here too, any type of apparatus can be used for the rotation of the support particles. The rate of rotation is important. This has to be sufficient to bring all surfaces of the support particles uniformly into contact with the alkaline fixing solution. It must not be so great that the insoluble metal compounds are rubbed off the support surface. The rotation rate should preferably be from 1 to 20 revolutions per minute, if desired greater, depending on the type of support material and the amount of metal which is to be precipitated on the support. The rotation rate also depends on the type of apparatus used, on the size and shape of the supports, on the type of supports, on the amount of metal with which they are treated, etc., but should correspond approximately to the abovementioned rotation rate.

The treatment in the second stage can be equivalent to that in the first stage, using a fixing solution of the same concentration. The total molar ratio of alkali metal to anion from the metal salt for both fixing stages together should preferably be from 1.1:1 to 3.3:1. Preference is given to using a borate solution as fixing solution in both stages.

Subsequent to the fixing step of method I or the last fixing step of method II, the supports are treated with a reducing agent in order to convert the precipitated noble metal salts and noble metal compounds present thereon into the metallic form. This reduction is carried out in the liquid phase, for example using aqueous hydrazine hydrate or an alkali metal borohydride, preferably sodium borohydride. The reduction is preferably carried out at room temperature. The reducing agent is added in excess so as to ensure that all the metal salts and metal compounds are converted into the metallic form. The boron compounds too may, depending on the type of reducing agent, be converted into elemental boron.

The support particles are washed, preferably with distilled water, in order to remove any chlorides still present in the support material which originate from the impregnation step and have been liberated by precipitation of the noble metals. Washing is continued until the chlorides have been removed from the support. Not more than 1000 ppm of chlorides should remain on the catalyst. To ensure the success of the washing procedure, the washings can be tested with silver nitrate solution. The washing procedure also serves to remove residues of reducing agent from step c). The catalyst is then dried at temperatures of at most 150° C., preferably in a stream of nitrogen or air.

Finally, addition of at least one alkali metal compound is necessary. The catalyst is preferably impregnated with an aqueous solution of potassium acetate and then dried. The potassium content of the finished catalyst is between 1 and 4% by weight, preferably between 1.5 and 3% by weight.

The preparation of the vinyl acetate is carried out by passing acetic acid, ethylene and oxygen or oxygen-containing gases over the finished catalyst at temperatures of from 100 to 220° C., preferably from 120 to 200° C., and at pressures of from 1 to 25 bar, preferably from 1 to 20 bar, with unreacted components being able to be recirculated. The oxygen concentration is advantageously kept below 10% by volume (based on the gas mixture free of acetic acid). However, dilution with inert gases such as nitrogen or carbon dioxide is sometimes advantageous. Carbon dioxide is particularly suitable for the dilution in a recirculation procedure since it is formed in small amounts during the reaction.

EXAMPLE 1

250 ml of silicon dioxide catalyst supports (manufactured by Sudchemie) in the form of spheres having a diameter of 7.3 mm were impregnated with 85 ml of an aqueous solution containing 4.6 g of $Na_2PdCl_4$ and 1.4 g of $NaAuCl_4$. The precipitation of the insoluble metal compounds was achieved by addition of 283 ml of an aqueous solution of 17 g of borax. The vessel was then immediately rotated by means of a rotary evaporator (without application of vacuum) for 2.5 hours at 5 revolutions per minute (rpm). The reduction was subsequently achieved by addition of 7 ml of hydrazine hydrate in 20 ml of water and immediate rotation of the vessel at 5 rpm for 1 hour. The supports thus treated were subsequently allowed to stand for 16 hours. The liquid was then poured off and the treated supports were washed with distilled water in order to remove the chloride ions. This required a water flow rate of 200 ml/minute for about 5 hours. The pellets thus obtained were dried for 1 hour at 100° C. The reduced catalyst was impregnated with an aqueous solution containing 10 g of potassium acetate and having a volume corresponding to the absorption capacity of the dry support material. The catalyst was then dried again.

200 ml of the finished catalyst were placed in a reaction tube having an internal diameter of 20 mm and a length of 1.5 m. The gas mixture to be reacted was then passed over the catalyst at a pressure of 8 bar at the reactor inlet and a wall temperature of 150° C. This gas mixture consisted of 50% by volume of ethylene, 12% by volume of acetic acid, 6% by volume of oxygen and 32% by volume of nitrogen. The results are shown in Table I.

COMPARATIVE EXAMPLE 1

The procedure of Example 1 was repeated, except that the precipitation of the insoluble metal compounds was effected by addition of 283 ml of an aqueous solution of 2 g of NaOH. The results are shown in Table I.

TABLE I

|  | Example 1 | Comparative Example 1 |
| --- | --- | --- |
| Output | 837 | 840 |
| Selectivities: |  |  |
| Carbon dioxide | 9.13 | 9.20 |
| Ethyl acetate | 0.09 | 0.12 |
| High-boilers | 0.58 | 1.53 |

Units:
Output: Gram of vinyl acetate per liter of catalyst per hour
Selectivities: Mol percent based on ethylene reacted

What is claimed is:

1. A catalyst for preparing vinyl acetate in the gas phase from ethylene, acetic acid and oxygen or oxygen-containing gases with, at the same time, low high-boiler formation, which catalyst consisting essentially of palladium 0.01 to 0.2% by weight of and/or its compounds, gold and/or its compounds, boron and/or its compounds and alkali metal compounds on a particulate support.

2. A catalyst as claimed in claim 1 comprising borates.

3. A catalyst as claimed in claim 1, wherein the alkali metal compound is potassium acetate.

4. A process for preparing a catalyst for producing vinyl acetate in the gas phase from ethylene, acetic acid and oxygen or oxygen-containing gases with, at the same time, low high-boiler formation, which catalyst consists essentially of palladium and/or its compounds, gold and/or its compounds and alkali metal compounds on a particulate support, where the catalyst is prepared by a) impregnating the support with soluble palladium and gold compounds;

b) converting the soluble palladium and gold compounds on the support into insoluble compounds by means of an alkaline solution;

c) reducing the insoluble palladium and gold compounds on the support by means of a reducing agent in the liquid phase;

d) washing and subsequently drying the support;

e) impregnating the support with a soluble alkali metal compound; and f) finally drying the support at a maximum of 150° C., wherein 0.01 to 0.2% by weight of boron or boron compounds are applied to the catalyst prior to the final drying.

5. The process as claimed in claim 4, wherein the alkaline solution used in step b) comprises boron compounds.

6. The process as claimed in claim 4, wherein the alkaline solution used in step b) comprises borates as boron compound.

7. The process as claimed in claim 4, wherein the reducing agent in the liquid phase used in step c) is an aqueous solution comprising hydrazine or an alkali metal borohydride.

8. The process as claimed in claim 4, wherein the reducing agent used in step c) is sodium borohydride.

9. The process as claimed in claim 4, wherein the soluble alkali metal compound used in step e) is potassium acetate.

10. A process for preparing vinyl acetate in the gas phase from ethylene, acetic acid and oxygen or oxygen-containing gases with, at the same time, low high-boiler formation over a catalyst as claimed in any of claim 1.

* * * * *